United States Patent
Yokoi

[11] Patent Number: 6,094,274
[45] Date of Patent: Jul. 25, 2000

[54] FLUORESCENCE DETECTING DEVICE

[75] Inventor: Eiji Yokoi, Hachioji, Japan

[73] Assignee: Olympus Optical Co., Ltd., Tokyo, Japan

[21] Appl. No.: 09/325,541

[22] Filed: Jun. 4, 1999

[30] Foreign Application Priority Data

Jun. 5, 1998 [JP] Japan .................................. 10-157986

[51] Int. Cl.$^7$ .................................................. G01N 21/64
[52] U.S. Cl. ........................ 356/417; 250/458.1; 359/389
[58] Field of Search .................................... 356/317, 318, 356/417; 250/458.1, 459.1, 461.1, 461.2; 359/389

[56] References Cited

U.S. PATENT DOCUMENTS 3,973,129  8/1976  Blumberg et al. ................... 250/461.2
5,371,624  12/1994  Nagano et al. ......................... 359/389

FOREIGN PATENT DOCUMENTS 9-15171  1/1997  Japan .

*Primary Examiner*—F. L. Evans
*Attorney, Agent, or Firm*—Pillsbury Madison & Sutro LLP

[57] ABSTRACT

The present invention provides a fluorescence detecting device comprising a light source, an excitation filter set, a dichroic mirror, an objective, an absorption filter set and an observation optical system, wherein the excitation filter set includes two interference films with a transmittance of 25% or more at a wavelength by 20 nm shorter than the cross-over wavelength when the wavelength at the crossing point between the transmittance spectrum at a longer wavelength side of the excitation filter set and the transmittance spectrum at a shorter wavelength side of the absorption filter set is defined as a cross-over wavelength, thereby enabling to obtain a bright fluorescent image with a very high S/N ratio without requiring a filter with higher precision.

16 Claims, 12 Drawing Sheets

FLUORESCENCE DETECTING DEVICE

BACKGROUND OF THE INVENTION

1. Field of the Invention

The present invention relates to a fluorescence detecting device to be used for observation and/or measurement of biological tissues and cells in the medical and biological fields.

2. Description of the Related Art

The fluorescent detecting device is usually used for detecting proteins and genes marked with a fluorescent marker on the biological tissues and cells in the medical and biological fields. Since observation of extremely weak fluorescence emitted from one molecule of a fluorescent dye has been required in recent years, further improvements in absolute brightness level and S/N ratio are desired.

FIG. 1 shows a basic construction of a conventional epi-illumination fluorescence microscope as a representative example of the fluorescent detecting device. In FIG. 1, the reference numerals 1 denotes a light source such as a mercury vapor lamp and the like, 2 denotes a collector lens, 3 denotes an aperture stop, 4 denotes a field stop, 5 denotes an excitation filter set, 6 denotes a specimen, 7 denotes a dichroic mirror, 8 denotes an objective, 9 denotes a stage, 10 denotes an absorption filter set, 11 denotes a beam splitter, 12 denotes a photography lens, and 13 denotes an observation optical system comprising an imaging lens and an ocular. While the luminous flux projected out of the light source 1 is condensed with the collector lens 2 and passes through the excitation filter set 5 via the aperture stop 3 and field stop 4, the light beam excitation light is converted into a luminous flux having a high intensity at only a desired excitation wavelength for the specimen 6. The luminous flux after passing through the excitation filter set 5 is reflected at the dichroic mirror 7 and irradiated to the specimen 6 on the stage 9 through the objective 8. The fluorescence emanated from the specimen 6 passes through the dichroic mirror 7 via the objective 8 and, after eliminating the light in unnecessary wavelength regions such as the illumination light with the absorption filter set 10 having a high transmittance at the desired fluorescence wavelength band, is guided to the photography lens 12 and observation optical system 13.

FIG. 2 and FIG. 3 show transmittance spectra of the excitation filter set 5 and absorption filter set 10, respectively, in the epi-illumination fluorescence microscope, wherein one kind of the fluorescent dye and two kinds of the fluorescent pigments are used in the experiments shown in FIG. 2 and FIG. 3, respectively. In the graphs, Ab1, Ab2 and Ab3 show transmission bands of the excitation filter sets 5, E1, E2 and E3 show transmission bands of the absorption filter sets 10, and F1, F2 and F3 show fluorescence emission bands. Since the excitation light arriving at the detector causes background noises that deteriorate S/N ratio to give a fluorescence image with low contrast, the transmission bands of E1 and Ab1 should not be almost overlapped with each other. These conditions are the same with respect to the transmission bands of E2, E3 and Ab2. While the wavelength where the transmittance spectrum of the excitation filter set 5 and the transmittance spectrum of the absorption filter set 10 cross with each other is termed a cross-over wavelength, the point X1 in FIG. 2, and the points X2, X3 and X4 correspond to this cross-over wavelength. Therefore, the S/N ratio of the fluorescence detecting device is determined by the width of the transmission wavelength band of the absorption filter set 10 and transmittance of each filter set at the cross-over wavelength.

Since most of the fluorescent dye have a fluorescence intensity peak at a wavelength very close to their excitation wavelength, it is crucial that the transmission wavelength bands of the excitation filter set and absorption filter set are very close with each other.

An epi-illumination laser fluorescence microscope making use of a laser light source has been practically used as a fluorescence detecting device. Since the wavelength of the light source is almost monochromatic and a wavelength that can effectively excite fluorescence with a desired wavelength is selected, no excitation filter set is needed in this device. The cross-over wavelength of the epi-illumination fluorescence microscope corresponds to the laser wavelength. The S/N ratio is determined by the width of the transmission wavelength band of the absorption filter set, its distance from the laser wavelength and transmittance of each filter set at the laser wavelength.

The S/N ratio of the fluorescence detecting device is largely influenced by the spectroscopic characteristics of the optical filters in the excitation filter set and absorption filter set. When the excitation light transmission wavelength band of the excitation filter set is made to come sufficiently close to the fluorescence transmission wavelength band of the absorption filter set while suppressing transmittance at the cross-over wavelength, detection with a high S/N ratio is realized along with enabling to obtain a sufficiently bright florescence image without intensifying the excitation light by efficiently detecting florescence, thereby allowing damages to the specimen and fading of the specimen due to the excitation light to be reduced. However, since the optical filter actually involves production errors, the transmission wavelength band of the excitation filter set is often separated from the fluorescence transmission wavelength band of the absorption filter set more than is necessary in order to prevent leaky illumination light at the cross-over wavelength even when the quality of the optical filter is a little distributed. Accordingly, obtaining a fluorescent image with a high S/N ratio has been difficult.

Examples for solving foregoing problems for realizing a fluorescence detecting device with a high S/N ratio are found in Japanese Unexamined Patent Publications No. Hei 5-188299 and No. Hei 9-15171. Japanese Unexamined Patent Publication No. Hei 5-188299 discloses an epi-illumination fluorescence microscope that always ensures an optimum observation of the fluorescence image without being affected by the production errors of the filter and conditions of the specimen, wherein the excitation filter and absorption filter composed of interference filters are supported in a rotatable manner around an axis being perpendicular to the optical axis, and the filters are cooperatively rotated with each other. A method for continuously changing the wavelength width and wavelength of the excitation light is disclosed in Japanese Unexamined Patent Publication No. Hei 9-15171, wherein the excitation filter is constructed by assembling an interference filter for transmitting long wavelength light and an interference filter for transmitting short wavelength light so that respective filters are able to rotate around an axis being perpendicular to the optical axis to form a tunable excitation light source.

Either methods disclosed in the patent publications above are making use of a phenomenon in which the transmission wavelength band of the interference filter continuously shifts toward a longer wavelength or shorter wavelength depending on the incident angle. The transmission wavelength band of the excitation filter is allowed to come close to the transmission wavelength band of the absorption filter while suppressing leaky light at the cross-over wavelength, because the excitation filter and absorption filter composed of interference filters are adjusted by allowing them to rotate around an axis perpendicular to the optical axis.

However, although characteristics of the filters are most effectively utilized in the method disclosed in Japanese Unexamined Patent Publications No. Hei 5-188299 and No. Hei 9-15171, the limits determined by the filter characteristics can be never surmounted. It is also evident that rising-up of the transmittance from the transmission band to the reflection band of the interference filter generally lose its steepness as the interference film is inclined from a plane perpendicular to the optical axis. FIG. 4 shows the characteristics of the interference filter, indicating the change of the transmittance spectrum against the tilt angle of the absorption filter against the plane perpendicular to the optical axis. As is evident from the graph, the S/N ratio may adversely affect the S/N ratio contrary to our expectation depending on the tilt angle of the filter and fluorescence emission wavelength band in the methods described in Japanese Unexamined Patent Publications No. Hei 5-188299 and No. Hei 9-15171. A considerable proportion of the important and currently available fluorescent dye have fluorescence intensity peak wavelengths very close to their the excitation wavelength bands. A detecting device capable of obtaining a bright image with as high a S/N ratio as possible is desired, because the conditions of the fluorescence detection have became very severe in recent years in the fluorescence observation of living cells, such that the intensity of the excitation light should be as weak as possible in order to reduce damages on the living specimen and fading of the specimen.

SUMMARY OF THE INVENTION

Accordingly, the object of the present invention is to provide a fluorescence detecting device capable of obtaining a bright fluorescent image with a very high S/N ratio.

Another object of the present invention is to provide a fluorescence detecting device that requires no high precision filters.

According to the present invention, the foregoing object can be attained by allowing the excitation light transmission wavelength band to come extremely close to the fluorescence transmission wavelength band while suppressing leaky light at the cross-over wavelength between the excitation filter set and absorption filter set.

In one aspect, the present invention provides a fluorescence detecting device provided with a light source, an illumination optical system for irradiating the light emitted from the light source to a specimen, an excitation filter set disposed in the illumination optical system for allowing a light with a specified wavelength region to transmit, a detecting optical system for detecting fluorescence emitted from the specimen, and an absorption filter set disposed in the detecting optical system for allowing the fluorescence to transmit, wherein the excitation filter set has at least two first interference films with a transmittance of 25% or more at a wavelength by 20 nm shorter than the cross-over wavelength, the absorption filter set has at least two second interference films with a transmittance of 50% or more at a wavelength by 20 nm longer than the cross-over wavelength, or the excitation filter set has at least two first interference filter films besides the absorption filter set has at least two second interference filter films to satisfy a condition of 0.05%<T<10% for the first and second interference filter films when the wavelength at the crossing point between the transmittance spectrum at a longer wavelength side of the excitation filter set and the transmittance spectrum at a shorter wavelength side of the absorption filter set is defined as a cross-over wavelength (T denotes the transmittance of the interference film at the cross-over wavelength).

The present invention also provides a fluorescence detecting device provided with a monochromatic or semi-monochromatic light source, an illumination optical system for irradiating the light emitted from the light source to a specimen, a detecting optical system for detecting fluorescence emitted from the specimen, and an absorption filter set disposed in the detecting optical system for allowing the fluorescence to transmit, wherein the shorter wavelength side of the fluorescence transmission wavelength band of the absorption filter set has at least two interference films with a transmittance of 50% or more at a wavelength by 20 nm longer than the central wavelength of the light source to satisfy a condition of 0.05%<$T_1$<10% ($T_1$ denotes the transmittance of the interference film at the central wavelength of the light source).

In another aspect, the present invention provides a fluorescence detecting device provided with a light source, an illumination optical system for irradiating the light emitted from the light source to a specimen, an excitation filter set disposed in the illumination optical system for allowing a light with a specified wavelength region to transmit, a detecting optical system for detecting fluorescence emitted from the specimen, and an absorption filter set disposed in the detecting optical system for allowing the fluorescence to transmit, wherein the excitation filter set has a plurality of excitation light transmission wavelength bands $\tau_i$ (n=1, 2, . . . , n), and the absorption filter set has a plurality of fluorescence wavelength bands $E_i$ (i=1, 2, . . . , n) corresponding to the excitation light transmission wavelength bands $\tau_1$, the excitation filter set having at least two first interference films with a transmittance of 25% or more at a wavelength by 20 nm shorter than the cross-over wavelength $\lambda_i$, the absorption filter set having at least two second interference films with a transmittance of 50% or more at a wavelength by 20 nm longer than the cross-over wavelength $\lambda_i$, or the excitation filter set having at least two first interference films besides the absorption filter set has at least two second interference films to satisfy a condition of 0.05%<$T_i$<10% or the first and second interference films, when the wavelength at the crossing point between the transmittance spectrum at a longer wavelength of an arbitrary excitation light transmission wavelength band $\tau_i$ and the transmittance spectrum at a shorter wavelength of the fluorescence transmission wavelength band $E_i$ corresponding to the arbitrary excitation light transmission wavelength band is defined as a cross-over wavelength $\lambda_i$ ($T_i$ denotes the transmittance of the interference film at the cross-over wavelength $\lambda_i$).

DETAILED DESCRIPTION OF THE PREFERRED EMBODIMENT

Prior to describing the embodiments in the present invention, the principle, function and effect of the present invention will be described.

When two filters having almost identical transmittance spectra are overlaid with each other, the transmittance spectrum of the piled filters generally exhibits squared characteristics of each filter. In other words, although few reduction of the transmittance is observed in the doubled filter as compared with the single filter in the wavelength band having a transmittance of about 100%, a sudden reduction of the transmittance is observed in the doubled filter as compared with the single filter in the wavelength bands having a transmittance of smaller than 100%. The slope of the transmittance spectra in the latter case becomes very steep as compared with that of the single filter. While this effect becomes evident as the number of the filters, or the filter faces, are increased, the excitation light transmitting wave band is made to come close to the fluorescence transmitting wave band in the present invention by utilizing this effect in a wavelength region within 20 nm of the wavelength band near the cross-over wavelength that requires a steep characteristic transmittance spectrum, or by utilizing the effect at the shorter wavelength side from the cross-over wavelength in the case of the excitation filter set or at the longer wavelength side from the cross-over wavelength in the case of the absorption filter set.

Figure 1:
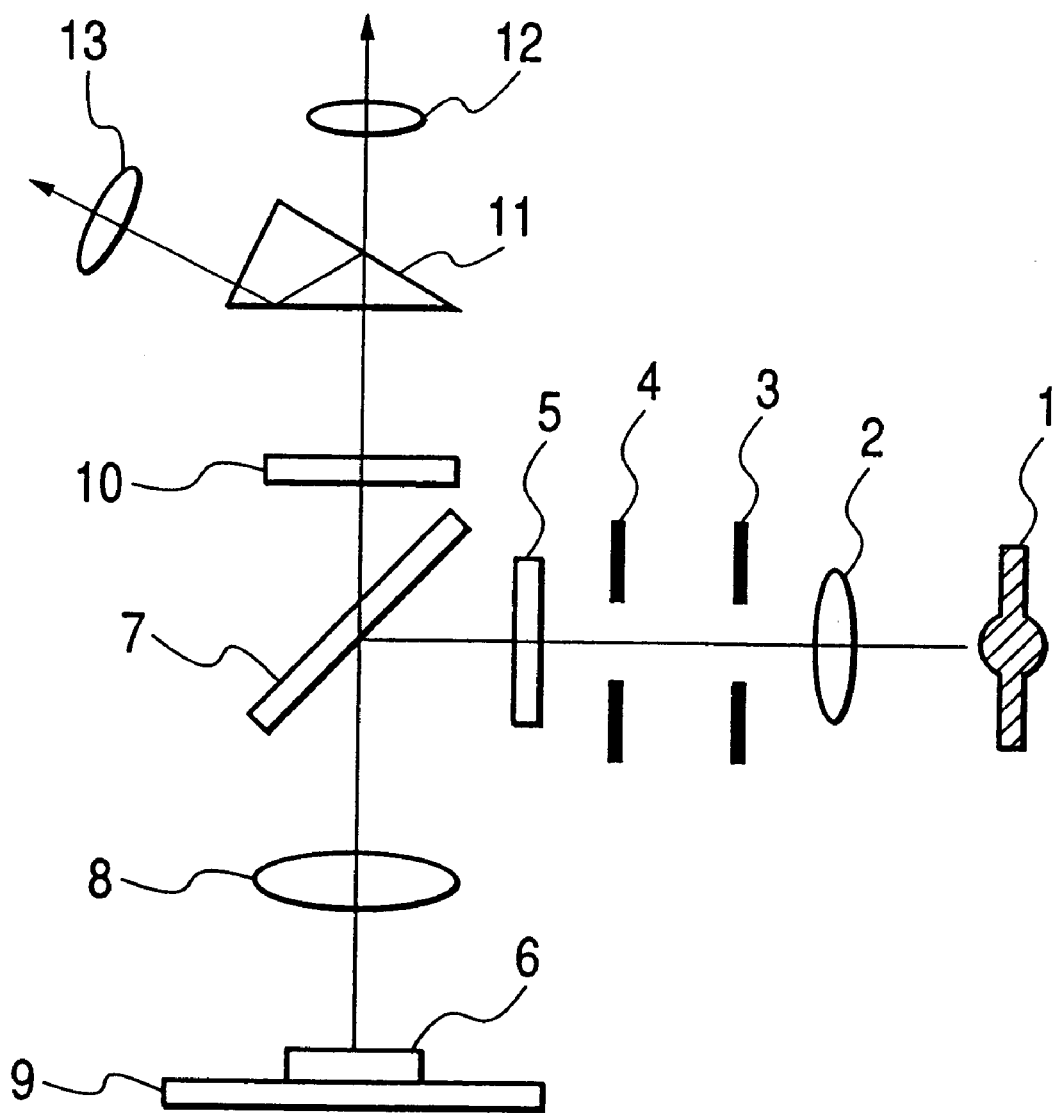
FIG. 1 shows an example of an optical construction of the conventional fluorescence detecting device.
Figure 2:
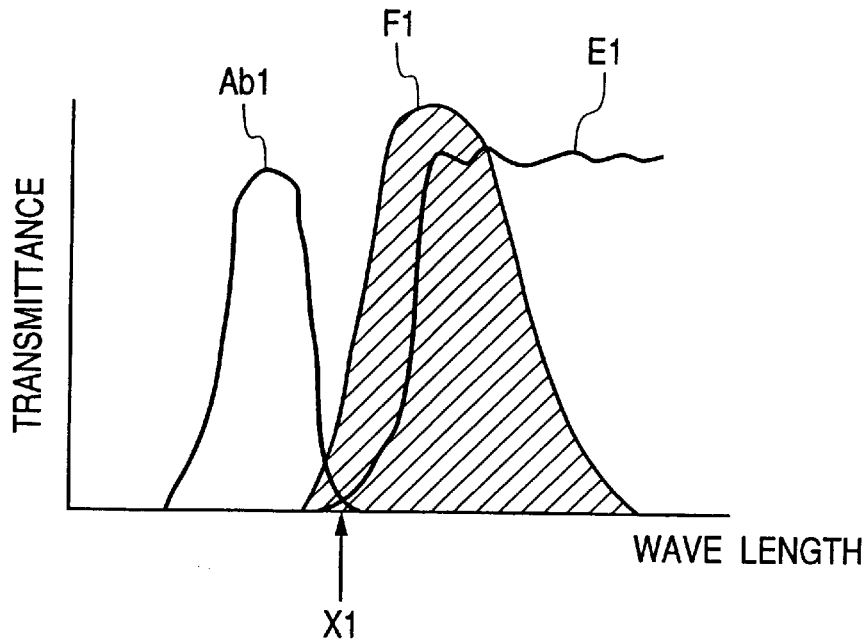
FIG. 2 shows an example of the transmittance spectra of the excitation filter set and absorption filter set to be used for the fluorescence detecting device illustrated in FIG. 1.
Figure 3:
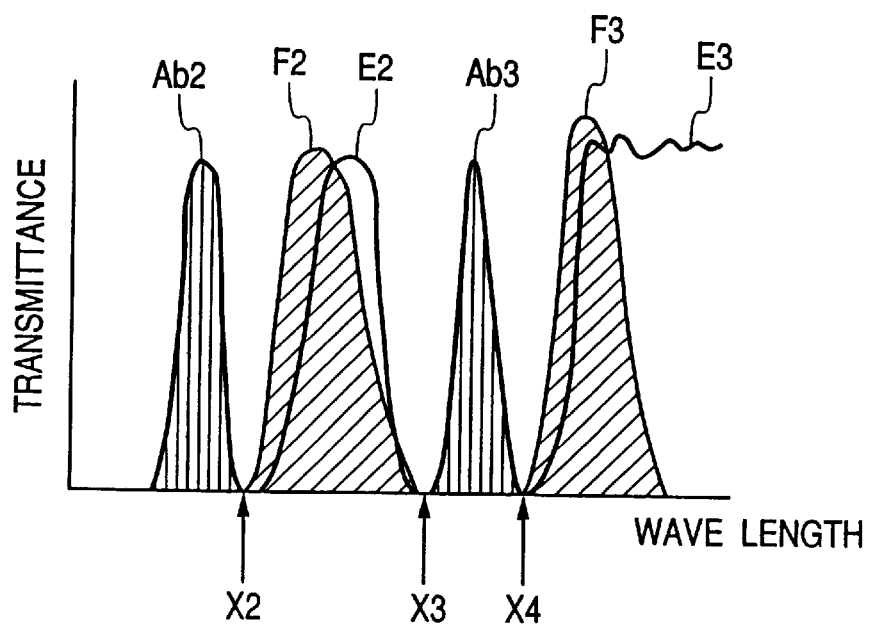
FIG. 3 shows an another example of the transmittance spectra of the excitation filter set and absorption filter set to be used for the fluorescence detecting device illustrated in FIG. 1.
Figure 4:
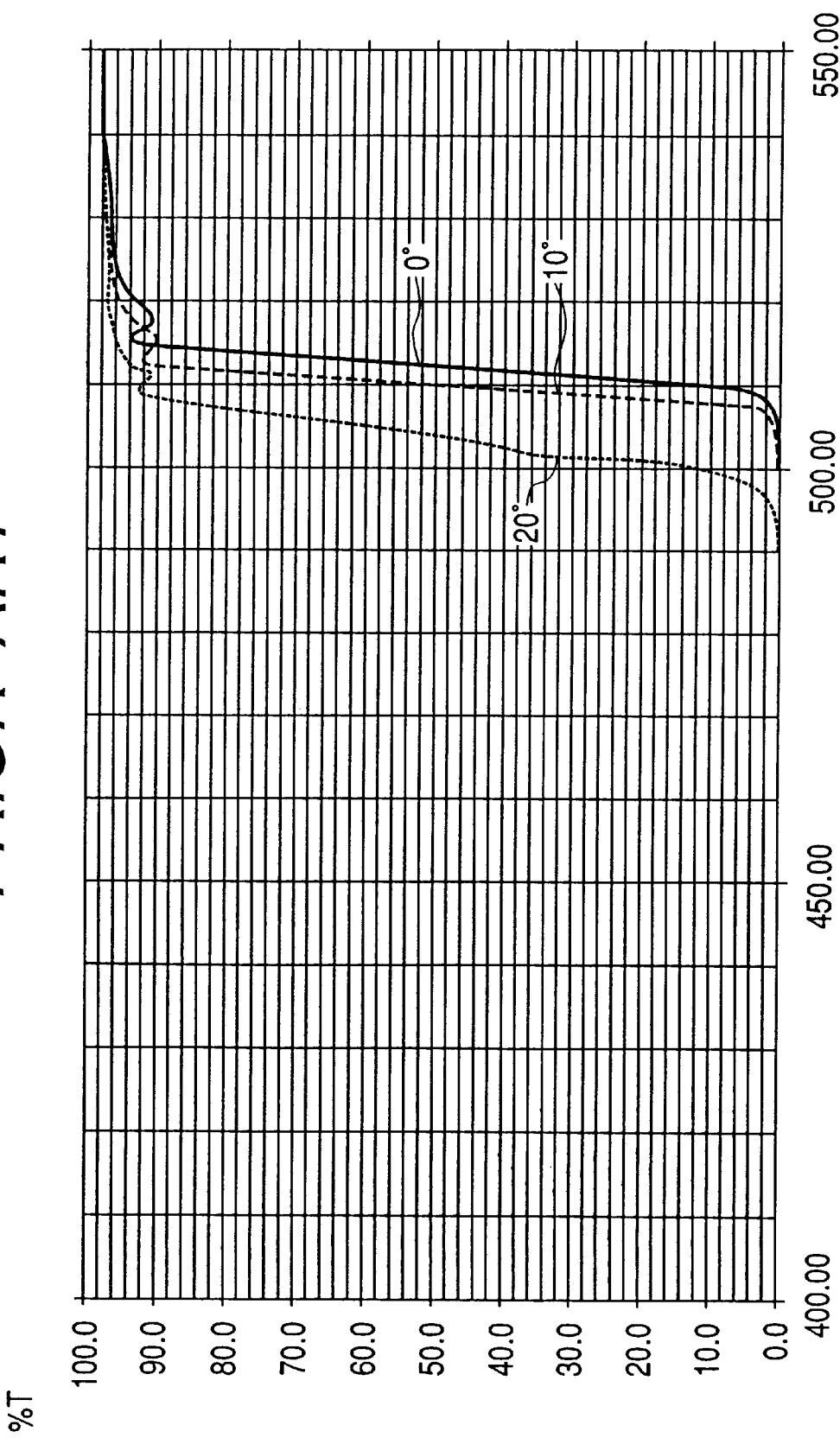
FIG. 4 shows the change of the transmittance spectrum against the light incident angle to the interference film.
Figure 5:
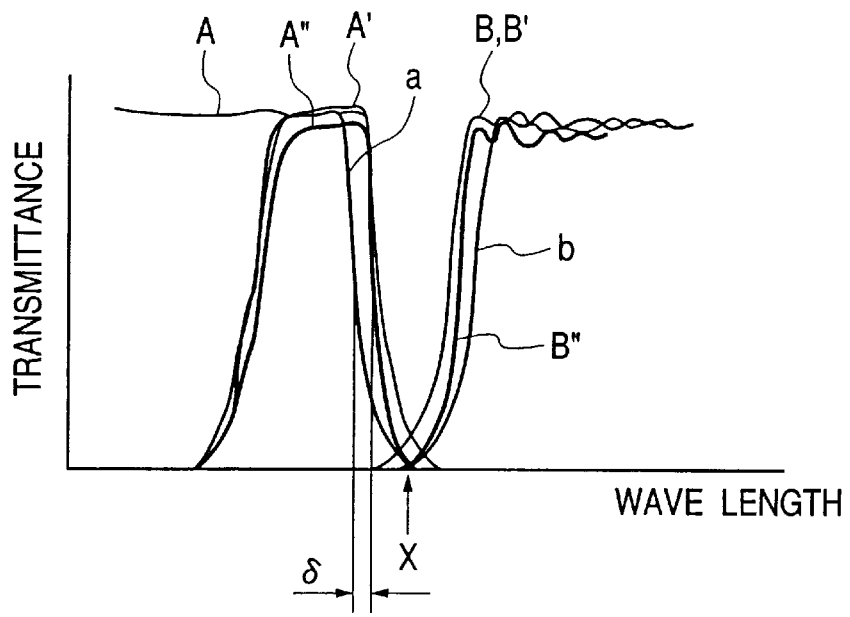
FIG. 5 shows characteristic transmittance spectra of the excitation filter set and absorption filter set according to the present invention in comparison with the conventional filters.
Figure 6:
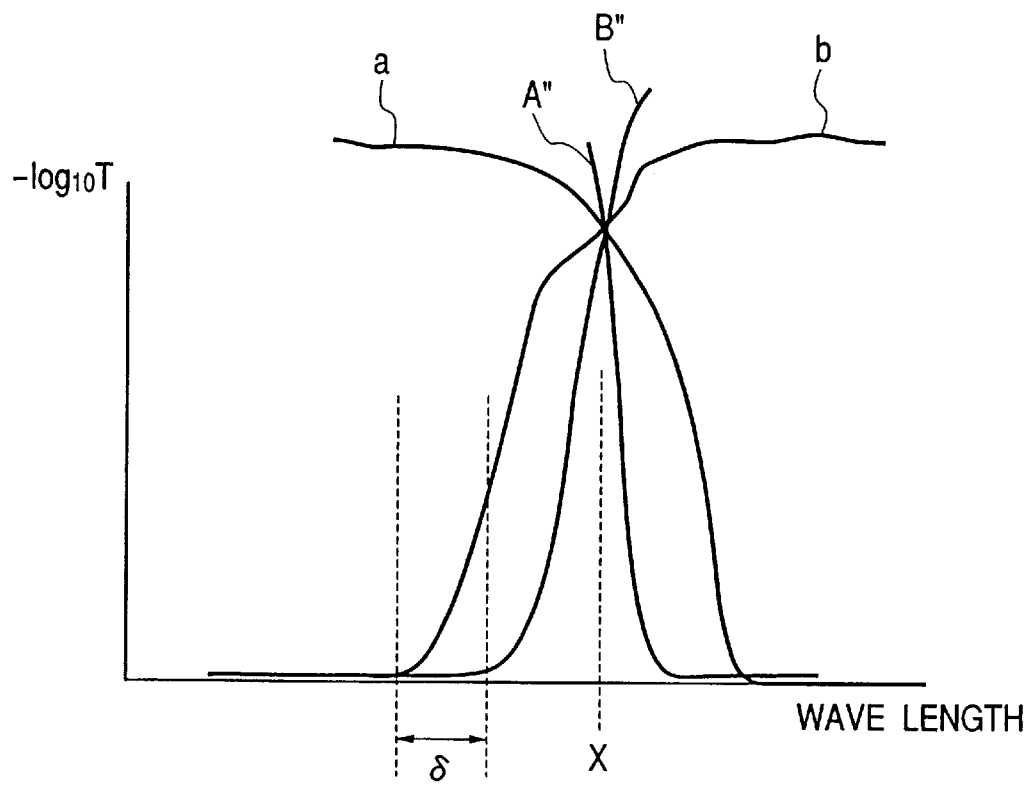
FIG. 6 shows characteristic spectra obtained by transferring the characteristic spectra shown in FIG. 5 into a logarithmic scale with a base of 10.

FIG. 5 shows characteristic transmittance spectra of the excitation filter set and absorption filter set as compared with the conventional filters, while FIG. 6 shows characteristic spectra obtained by transferring the characteristic spectra shown in FIG. 5 into a logarithmic scale with a base of 10. Transmittance spectra of the two interference films A and A' disposed in the illumination optical paths are denoted by A and A', respectively, and those of the two interference films B and B' disposed in the detection optical path are denoted by B and B', respectively, in the graph. The transmittance spectrum of the excitation filter set A" having the interference films A and A' is denoted by A" and that of the absorption filter set B" having the interference films B and B' is denoted by B" in the graph. The transmittance spectrum of the conventional excitation filter set a is denoted by a, and that of the conventional absorption filter set b is denoted by b in the graph. The cross-over wavelength is denoted by x.

While the excitation filter set A" and absorption filter set B" are the filter sets used in the present invention, transmittance rises up in a narrow wavelength region from the cross-over wavelength x when the transmittance spectra of the filter sets A" and B" are compared with the transmittance spectra of the conventional filter sets a and b, because the rise-up portions of the interference films A and A', and the rise-up portions of the interference films B and B' are taking advantage of the squared characteristics with respect to transmittance as described above. Consequently, the excitation light transmitting band comes close to the fluorescence transmitting band by a wavelength δ as compared with the conventional filter set with the proviso that transmittance of each filter set at the cross-over wavelength remains unchanged. Accordingly, more fluorescence can be detected as the fluorescence transmitting band is expanded toward the excitation wavelength side, enabling to expect a large improvement of the S/N ratio. Both of the interference faces A, A' and B, B' are not always needed, but either one of them can exert a sufficient effect. Transmittance of the filter set acceptable at the cross-over wavelength be expressed by T, then transmittance required for the interference films A, A' and B, B' may be about a square root of transmittance of the conventional films, or be expressed by $T^{1/2}$, indicating that the interference film according to the present invention is quite advantageous in the production cost and yield of the filter. When a transmittance of T=0.01% is required, for example, one filter may have a transmittance of 1%.

However, when transmittance of the interference films A, A' and B, B' at the cross-over wavelength becomes lower than 0.05%, the excitation light is excessively cut off and the advantageous effect of the present invention—allowing the fluorescence transmission wavelength band to come close to the excitation light transmission wavelength band—can not be fully displayed, thus failing to expect improvement of the S/N ratio. When transmittance of the interference films A, A' and B, B' at the cross-over wavelength exceeds 10%, the S/N ratio is decreased because the illuminating light is not sufficiently cut off.

When a monochromatic light or semi-monochromatic light is used, the excitation filter set is not needed because the wavelength that can effectively excite the given fluorescent dye is selected. Alternatively, a filter set that can exclude the illuminating light to allow fluorescence to pass through with a high transmittance may be disposed in the detection light path. The wavelength of the light source as described above may be considered to be a cross-over wavelength provided that the cross-over wavelength serves as a wavelength that allows the leaky light arriving at the detector to be maximum. The same effect as described above can be expected when the light source wavelength is replaced with the cross-over wave length. In other words, the fluorescence transmission wavelength band may be expanded toward the wavelength side of the light source by disposing at least two interference films having a transmittance of 50% or more at a wavelength by 20 nm longer than the central wavelength of the light source, enabling to largely improve the S/N ratio.

Figure 7:
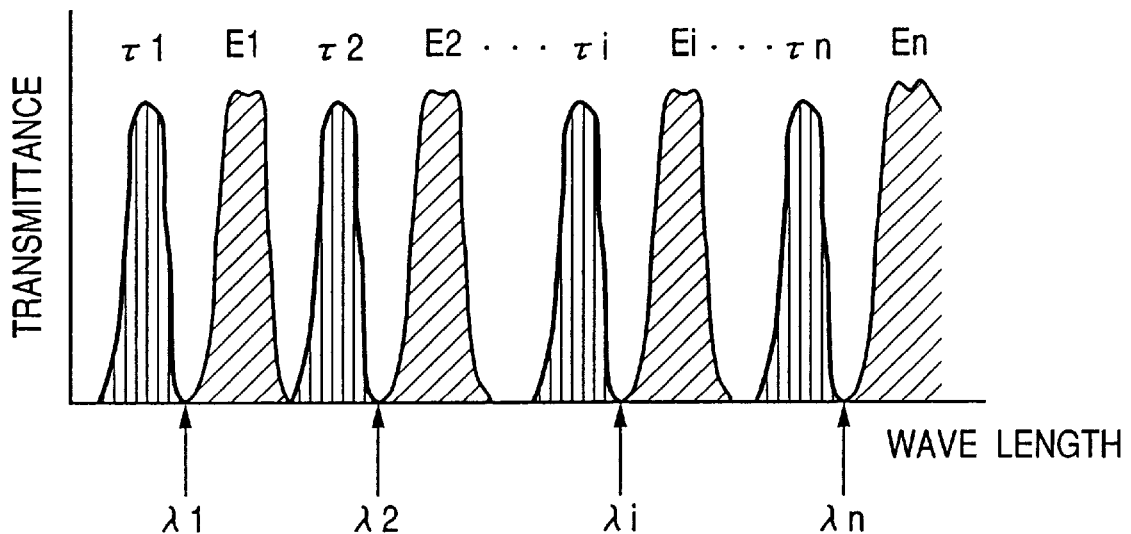
FIG. 7 shows characteristic transmittance spectra of the excitation filter set and absorption filter set when a plurality of fluorescence wavelength bands excited by a plurality of excitation wavelength bands are fluorometrically detected.
Figure 8:
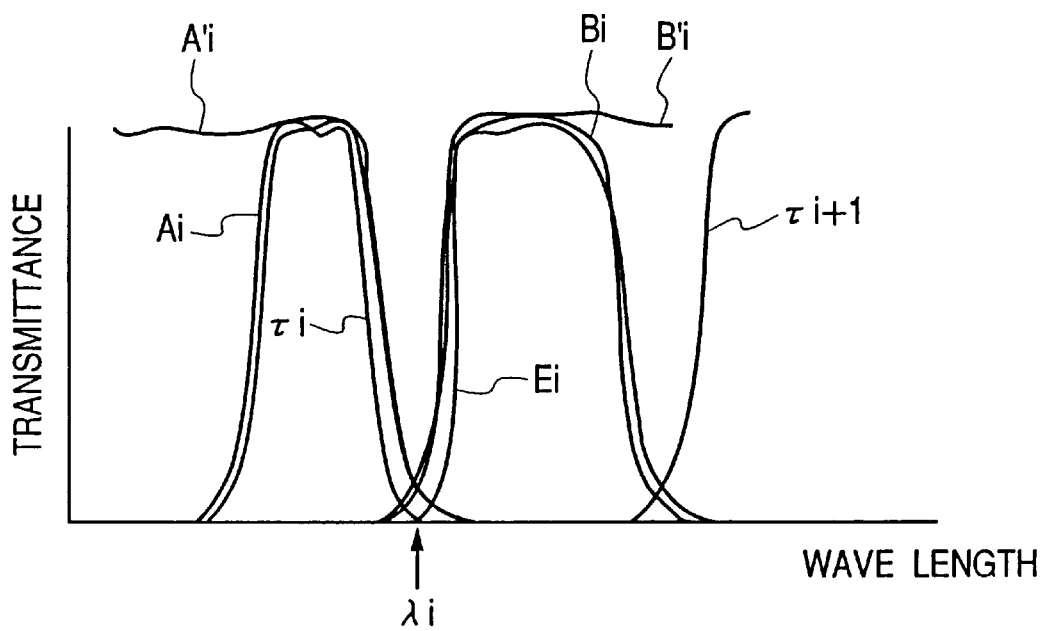
FIG. 8 shows transmittance spectra of the i-th excitation light transmission wavelength band and i-th fluorescence transmission wavelength band.

Detection of fluorescence of a plurality of fluorescence wavelength bands excited by a plurality of excitation light wavelength bands is also possible according to the present invention. FIG. 7 shows the characteristic transmittance spectra of the excitation filter set and absorption filter set while FIG. 8 shows the transmittance spectra of the i-th excitation light transmission wavelength band $\tau_i$ and i-th fluorescence transmission wavelength band $E_i$. Denoted by $\lambda_i$ in the graph is the crossing wavelength of the transmittance spectra in the fluorescence transmission wavelength band $E_i$ excited with the excitation light transmission wavelength band $\tau_i$ and with the light in the excitation light transmission wavelength band. Denoted by $A_i$ and $A_i'$ are at least two interference films constituting the excitation filter set having a transmittance of 25% or more at a wavelength by 20 nm shorter than the wavelength $\lambda_i$, and the transmittance spectrum of the filter set. Denote by $B_i$ and $B_i'$ are at least two interference films constituting the absorption filter set having a transmittance of 50% or more at a wavelength by 20 nm longer than the wavelength $\lambda_i$, and the transmittance spectrum of the filter set.

The given fluorescence excited with a light in any of the first to n-th excitation light transmission wavelength band $\tau_i$ is detected after passing through a fluorescence transmission wavelength band $E_i$. Take notice of an arbitrary i-th excitation light transmission wavelength band $\tau_i$ and fluorescence transmission wavelength band $E_i$ as shown in FIG. 8, then the functions and effects of them are as described previously. In other words, the given fluorescence can be effectively detected by expanding the excitation transmission wavelength band or fluorescence transmission wavelength band toward the cross-over wavelength side. The interference films $A_i$, $A_i'$ and $B_i$, $B_i'$ are not always needed to be fitted to the same i-th excitation light transmission wavelength band $\tau_i$ and fluorescence transmission wavelength band $E_i$, or these interference filter sets are not necessarily disposed on both excitation filter sets and absorption filter sets, but a sufficient improvement of the S/N ratio is possible by disposing the filter set on either the excitation filter set or the absorption filter set. Also, not all the interference films are required to be simultaneously inserted into the luminous flux or into the fluorescence luminous flux in the excitation filter set and absorption filter set, but at least the interference film constructing the i-th fluorescence transmission wavelength band may be disposed in the fluorescence luminous flux when the interference film constituting the i-th excitation light transmission band is disposed in the luminous flux.

Figure 9:
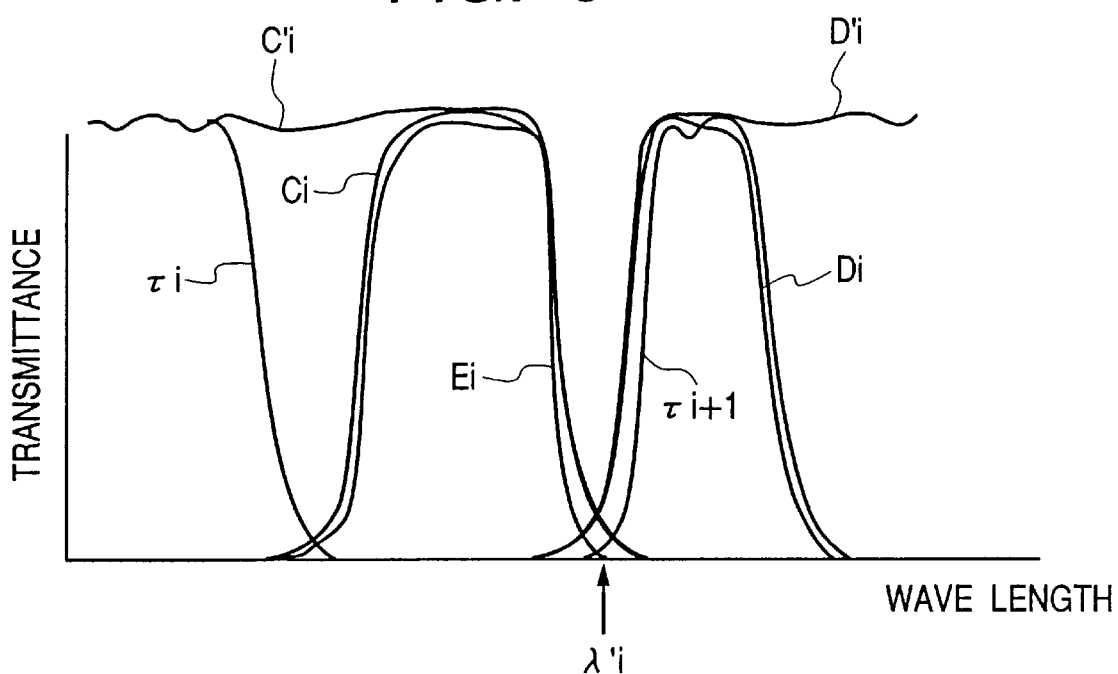
FIG. 9 shows transmittance spectra of the (i+1)-th excitation light transmission wavelength band and i-th fluorescence transmission wavelength band.

The S/N ratio can be improved by allowing the fluorescence transmission wavelength band $E_i$ to expand toward the excitation light transmission wavelength band $\tau_i+1$, instead of allowing the excitation light transmission wavelength band $\tau_i$ to come close to the fluorescence transmission wavelength band $E_i$. FIG. 9 shows the transmittance spectra of the (i+1)-th excitation light transmission wavelength band $\tau_i+1$ and i-th fluorescence transmission wavelength band $E_i$. In the graph, $\lambda'_i$ denotes the crossing wavelength of the transmittance spectra at the transmission wavelength band $E_i$ excited with the light in the (i+1)-th excitation light transmission wavelength band $\tau_i+1$ and i-th excitation light transmission wavelength band $\tau_i$ (i=1, 2, ..., n-1). Denoted by $C_i$ and $C'_i$ are at least two interference films constituting the excitation filter set having a transmittance of 25% or more at the wavelength by 20 nm longer than the wavelength $\lambda'_i$ and their transmittance spectra. Denoted by $D_i$ and $D'_i$ are at least two interference films constituting the absorption filter set having a transmittance of 50% or more at the wavelength by 20 nm shorter than the wavelength $\lambda'_i$ and their transmittance spectra. As is evident from FIG. 9, the cross-over wavelength $\lambda'_i$ should be made to come as close to the excitation light transmission wavelength band $\tau_i+1$ as possible or the i-th fluorescence transmission wavelength band $E_i$ should be made to come as close to the cross-over wavelength $\lambda'_i$ in order to expand the i-th fluorescence transmission wavelength band $E_i$, since the central wavelength of the excitation light transmission wavelength band $\tau_i+1$ remains unchanged. The i-th fluorescence transmission wavelength band $E_i$ is allowed to be expanded in the present invention by the squared effect brought about by placing the foregoing interference film over the interference films $C_i$, $C'_i$ and $D_i$, $D'_i$, thereby enabling detection of fluorescent images with a high S/N ratio.

EXAMPLES

The present invention will now be described by way of examples shown in the attached drawings.

Example 1

Figure 10:
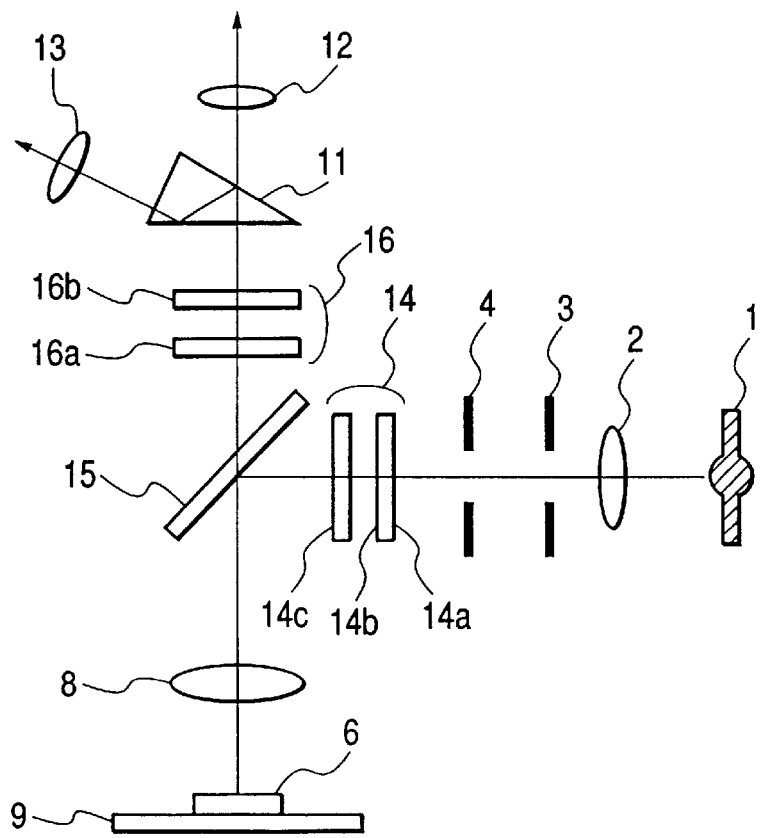
FIG. 10 shows an optical construction diagram in the first embodiment of the fluorescence detecting device according to the present invention.
Figure 11:
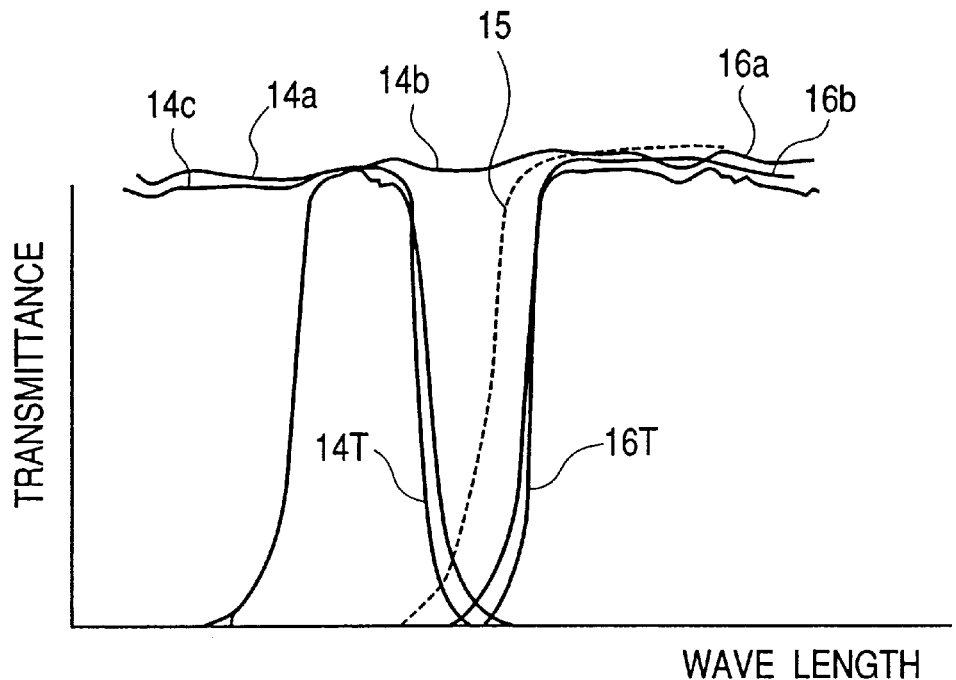
FIG. 11 shows transmittance spectra of the excitation filter set and absorption filter set in the first embodiment.

FIG. 10 shows the optical construction of the epi-illumination fluorescence microscope as one example of the fluorescence detecting device according to the present invention. The substantially same optical members as used in the conventional examples are attached with the same reference marks or numerals. FIG. 11 shows the transmittance spectra of the excitation filter set 14, dichroic mirror 11 and absorption filter set 16 as used herein. The excitation filter set 14 has a first interference film 14a, the second interference film 14b and the third interference film 14c in this embodiment, forming an excitation light transmission wavelength band 14T. The transmission wavelength of the excitation light transmission wavelength band 14T at the longer wavelength side is determined by the interference films 14a and 14c while the excitation light transmission wavelength band 14T at the shorter wavelength side is determined by the interference film 14b. Both of the interference films 14a and 14c have a transmittance of 90% and a transmittance of 5% at a wavelength by 20 nm shorter than the cross-over wavelength and at the cross-over wavelength, respectively. Respective interference films are disposed in non-parallel relation with each other. The absorption filter set 16 has, on the other hand, the first interference film 16a and second interference film 16b, forming the fluorescence transmission wavelength band 16T. Both of the interference films 16a and 16b have a transmittance of 80% and a transmittance of 5% at a wavelength by 20 nm longer than the cross-over wavelength and at the cross-over wavelength, respectively. Respective interference films are disposed in non-parallel relation with each other.

The luminous flux emanated from the light source 1 is condensed with the collector lens 2 and passes through the excitation filter set 14 via the aperture stop 3 and field stop 4. The luminous flux after passing through the excitation filter set 14 is projected onto the dichroic mirror 15. Since the dichroic mirror 15 has characteristic transmission spectra as shown in FIG. 11, the luminous flux after passing through the excitation filter set 14 is reflected on this dichroic mirror 15 and, after passing through the objective 8, is irradiated onto the specimen 6 on the stage 9. Fluorescence emitted from the specimen 6 is entered into the dichroic mirror 15 via the objective 8. The dichroic mirror 15 allows the fluorescence excited by the luminous flux after passing through the excitation light transmission wavelength band 14T of the excitation filter set 14 to pass through, allowing it to enter into the succeeding absorption filter set 16. Unnecessary wavelength such as in the illumination light is removed with this absorption filter set, allowing merely the desired fluorescence to be guided to the photography lens 12 and observation optical system 13.

As described above, the fluorescence transmission wavelength band is expanded toward the excitation wavelength side besides sufficiently excluding the illumination light by making the rising-up characteristics of the transmittance from the cross-over wavelength to be steep using both of the excitation filter set 14 and absorption filter set 16 in the present embodiment, enabling to efficiently detect the fluorescence with a high S/N ratio.

Example 2

Figure 12:
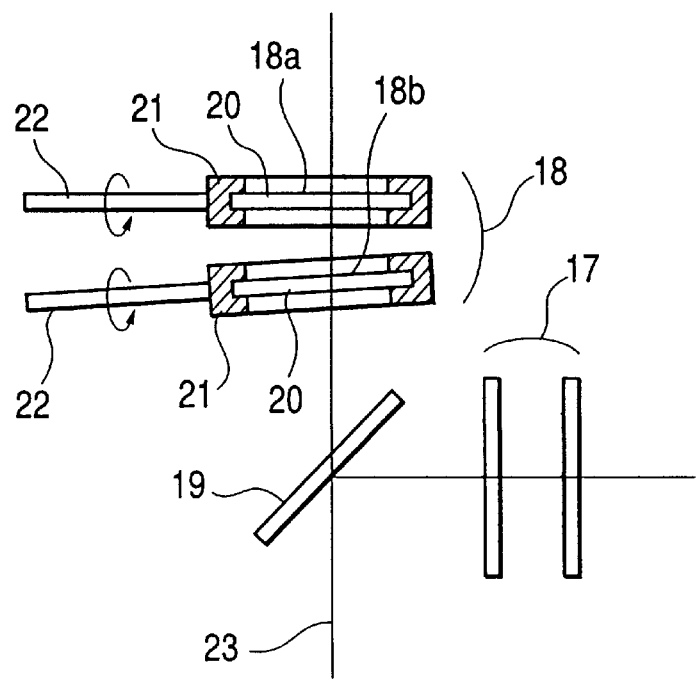
FIG. 12 shows a main part of the construction in the second embodiment of the fluorescence detecting device according to the present invention.

FIG. 12 shows the main part of the construction in the second embodiment of the fluorescence detecting device according to the present invention, in which other constructions are omitted since they are the same as in the first embodiment shown in FIG. 10. The reference numerals 17, 18 and 19 denote the excitation filter set, absorption filter set and dichroic mirror, respectively. The excitation filter set 18 is composed of the interference films 18a and 18b each being formed on two glass substrates 20 having parallel planes with each other, and respective glass substrates 20 is fixed on respective substrate holding frames 21 having a filter rotation member 22. A pair of the filter rotation members 22 are elongated along the direction parallel to the respective glass substrates 20, and the former and the latter are disposed to be in non-parallel relation with each other. Accordingly, while the tilt angle of each of the interference films 18a and 18b is changed against the face perpendicular to the observation axis 23 when each filter rotation member 22 is rotated, they are never placed in parallel relation with each other.

Figure 13:
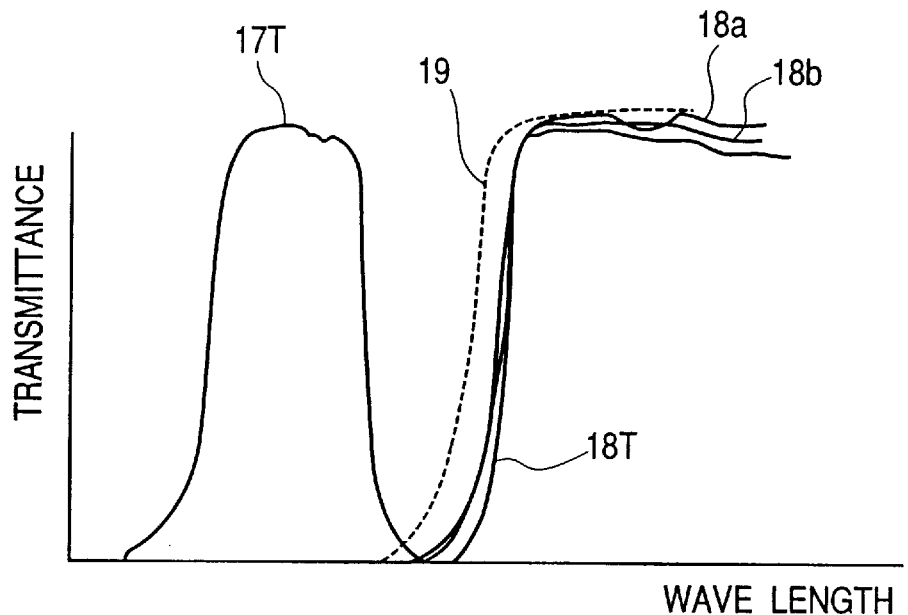
FIG. 13 shows transmittance spectra of the excitation filter set, absorption filter set and dichroic mirror in the second embodiment.

FIG. 13 shows the transmittance spectrum 17T of the overall excitation filter set 17, the transmittance spectrum 18T of the overall absorption filter set 18, the transmittance spectrum of the first interference film 18a and the second interference film 18b of the absorption filter set 18. Both of the interference films 18a and 18b have a transmittance of 80% at the wavelength by 20 nm longer than the cross-over wavelength and a transmittance of 1% at the cross-over wavelength.

Accordingly, the present embodiment allows the fluorescence transmission wavelength band to be expanded toward the fluorescence transmission wavelength band while sufficiently excluding the wavelength in the illumination light by making rise-up characteristics of transmittance from the cross-over wavelength of the absorption filter set steep, enabling to efficiently detect fluorescence. Since the fluorescence transmission wavelength can be adjusted toward the longer or shorter wavelength by changing the tilt angles of the interference films 18a and 18b against the face perpendicular to the observation optical axis 23, production errors of the characteristic spectra of the interference films 18a and 18b, and distribution of the transmittance spectrum of the excitation filter set 17 can be corrected to optimize the S/N ratio.

Example 3

Figure 14:
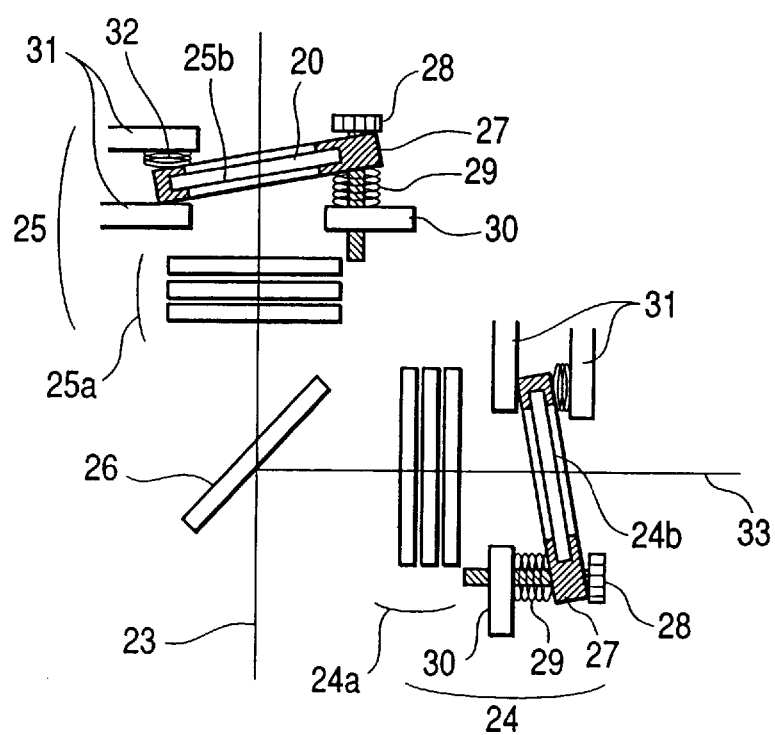
FIG. 14 shows a main part of the construction in the third embodiment of the fluorescence detecting device according to the present invention.

FIG. 14 shows the main part of the construction in the second embodiment of the fluorescence detecting device according to the present invention, in which other constructions are omitted since they are the same as the first embodiment shown in FIG. 10. The reference numerals 24, 25 and 26 in the drawing denote the excitation filter set, absorption filter set and dichroic mirror, respectively. The excitation filter set 24 is composed of a group of the fixed filters 24a comprising a plurality of filters disposed in parallel relation with each other, and a movable interference film 24b. The absorption filter set 25 is also composed of a group of the fixed filters 25a comprising a plurality of filters disposed in parallel relation with each other, and a movable interference film 25b. The interference films 24b and 25b are formed on a glass substrate 20 as in the second embodiment and they are attached to a substrate holding frame 27. One end of the substrate holding frame 27 is attached to a filter fix frame 30 with a screw 28 via a spring 29, while confronting the other end is press-adhered to a filter fix frame 31 with a spring 32. The screw 28 is movable forward and backward by varying its degree of fastening or loosening into the filter fix frame 30. The reference numeral 33 denotes the illumination optical axis.

Figure 15:
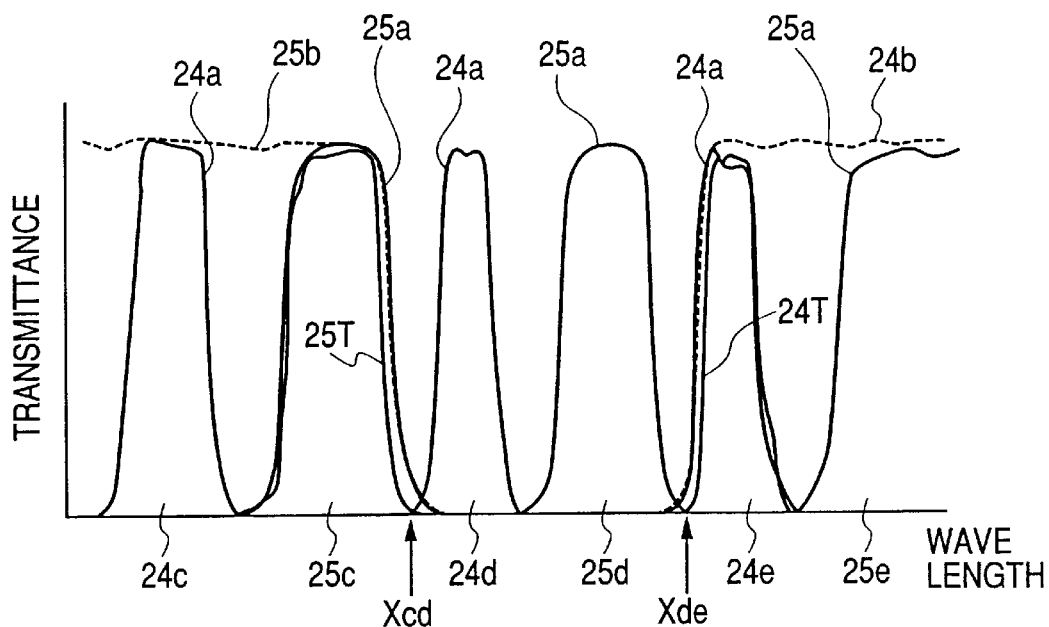
FIG. 15 shows transmittance spectra of the excitation filter set and absorption filter set in the third embodiment.

FIG. 15 denotes the transmittance spectrum of each filter in the present embodiment. The transmittance spectrum 24T of the overall excitation filter sets 24 is composed of respective transmittance spectra of the filter group 24a and interference film 24b, and contains the excitation transmission wavelength bands 24c, 24d and 24e for exciting the first, second and third fluorescence viewed from the shorter wavelength side, respectively. Since the transmittance through the interference film 24a and transmittance through the interference film 24b are 5% and 8% at the cross-over wavelengths Xde between the fluorescence transmission wavelength band 25d and excitation light transmission wavelength band 24e, and 80% and 85% at the wavelength by 20 nm longer than the cross-over wavelengths Xde, the fluorescence transmission wavelength band 25d is expanded toward the excitation light transmission wavelength band 24e side, enabling to efficiently detect fluorescence with a high S/N ratio. Also, since the characteristic transmittance spectra are able to be adjusted toward longer or shorter wavelength by changing the tilt angle of the interference film 24b against the face perpendicular to the illumination optical axis 33 by rotating the screw 28, distribution of the characteristic transmittance spectra of the interference film 24b is corrected to optimize the S/N ratio.

The transmittance spectrum 25T of the overall absorption filter set 25 is composed of respective transmittance spectra of the filter group 25a and interference film 25b, containing three fluorescence transmission wavelength bands 25c, 25d and 25e corresponding to three fluorescence wavelengths excited with the light from the three excitation light transmission wavelength bands 24c, 24d and 24e. The transmittance spectrum of the filter group 25a and that of the interference film 25b are each 3% at the cross-over wavelength Xcd between the fluorescence transmission wavelength band 25c and excitation light transmission wavelength band 24d, and 90% and 85% at the wavelength by 20 nm shorter than the cross-over wavelength Xcd, respectively. Accordingly, the fluorescence transmission wavelength band 25c can be expanded toward the excitation light transmission wavelength bands 24d while sufficiently excluding the wavelength in the illumination light, enabling to efficiently detect fluorescence with a high S/N ratio. Since the characteristic transmittance spectra can be adjusted toward the longer or shorter wavelength by changing the tilt angles of the interference films 25b against the face perpendicular to the observation optical axis 23 by rotating the screw 28, production errors of the characteristic spectra of the interference films 25b can be corrected to optimize the S/N ratio.

Example 4

Figure 16:
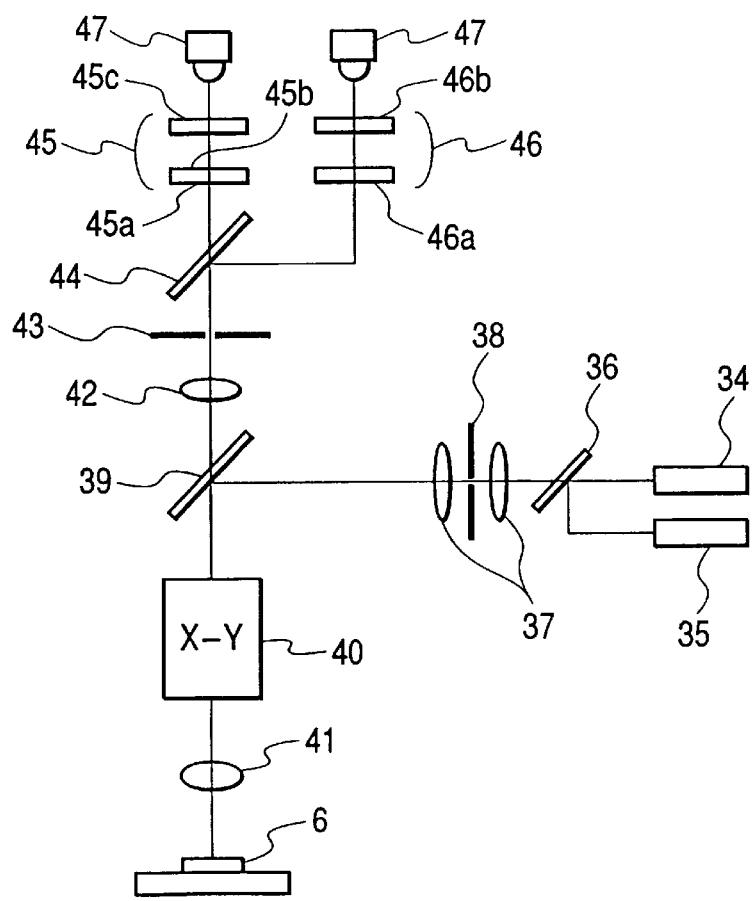
FIG. 16 shows an optical construction of the fluorescence detecting device in the fourth embodiment according to the present invention.
Figure 17:
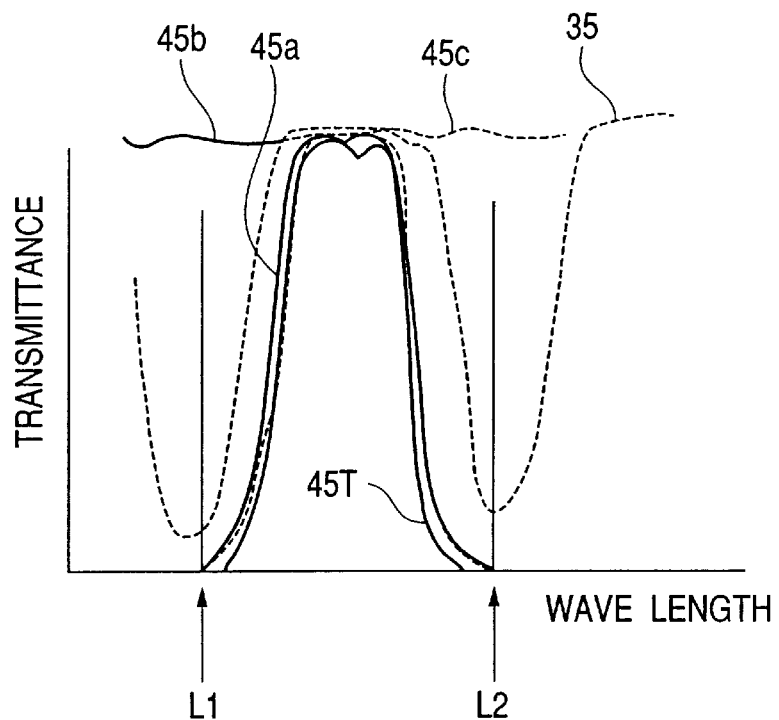
FIG. 17 shows transmittance spectra of the first absorption filter set and dichroic mirror in the fourth embodiment.

FIG. 16 shows the optical construction of the laser scanning epi-illumination fluorescence microscope in the fourth embodiment according to the present invention. The reference numerals 34 and 35 denotes laser sources having different oscillation wavelengths with each other, the reference numeral 36 denotes a dichroic mirror for mixing laser lights, the reference numeral 37 denotes a beam expander, the reference numeral 38 denotes a spatial filter, the reference numeral 39 denotes a dichroic mirror having the characteristic transmittance spectra as shown in FIG. 17, the reference numeral 40 denotes a X-Y scanner for scanning the specimen 6 in two dimensions, the reference numeral 41 denotes an objective, the reference numeral 42 denotes an image forming lens, the reference numeral 43 denotes a pin-hole, the reference numeral 44 denotes a dichroic mirror for isolating the first fluorescent light excited at a wavelength L1 of the laser source 34 from the second fluorescent light excited at a wavelength L2 of the laser source 35, the reference numeral 45 denotes the first absorption filter set, the reference numeral 46 denotes the second filter set and the reference numeral 47 denotes an optical detector such as a photomultiplier. The filter set 45 comprises the interference films 45a, 45b and 45c formed on the glass substrate, and the filter set 46 comprises the interference films 46a and 46b formed on the glass substrate.

The luminous flux emanated from the laser sources 34 and 35 are combined with the dichroic mirror 36. The combined luminous flux is entered into the dichroic mirror 39 via the beam expander 37 and spatial filter 38, is reflected there, passes through the X-Y scanner 40 and objective 41, and is irradiated onto the specimen 6. Accordingly, the fluorescent light emitted from the specimen 6 passes through the dichroic mirror 39 via the objective 41 and X-Y scanner 40, and condensed on the pin-hole 43 through the image forming lens 42. The fluorescent light that has passed through the pin-hole 43 is condensed on the pin-hole 43, and is divided into two optical paths with the dichroic mirror 44. The first and second fluorescent lights after blocking the lights having wavelengths in the light source or other fluorescent light are detect by the optical detector 47.

Figure 18:
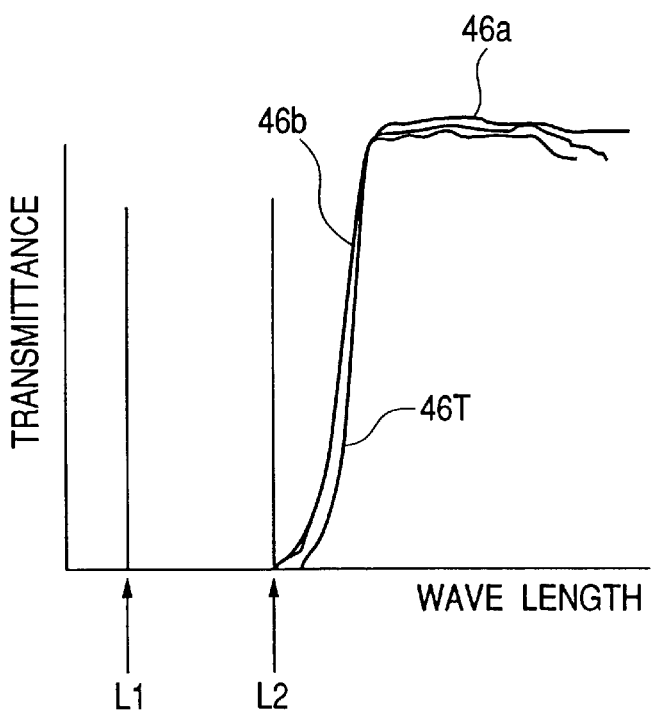
FIG. 18 shows transmittance spectra of the second absorption filter set in the fourth embodiment.

The transmittance spectra of the absorption filter set 45 and absorption filter set 46 are shown in FIG. 17 and FIG. 18, respectively. The reference numeral 45T denotes the transmittance spectrum of the overall filter set 45. The interference films 45a and 45b have a transmittance of 90% at a wavelength by 20 nm shorter than the second laser wavelength L2 and a transmittance of 1% at the wavelength L2, and the interference films 45a and 45c have a transmittance of 90% at a wavelength by 20 nm longer than the first laser wavelength L1 and a transmittance of 1% at the wavelength L1. Accordingly, the fluorescence transmission wavelength band of the absorption filter set 45 is expanded toward both wavelength sides of the laser wavelengths L1 and L2, enabling to quite effectively detect the first fluorescence with a high S/N ratio. The reference numeral 46T denotes a transmittance spectrum of the overall absorption filter set 46. The interference films 46a and 46b have a transmittance of 90% at the wavelength by 20 nm longer than the laser wavelength L2 and a transmittance of 1% at the wavelength L2. Accordingly, the fluorescence transmission wavelength band of the absorption filter set 46 is expanded toward the laser wavelength L2, enabling to quite effectively detect the first fluorescence with a high S/N ratio.

Example 5

Figure 19:
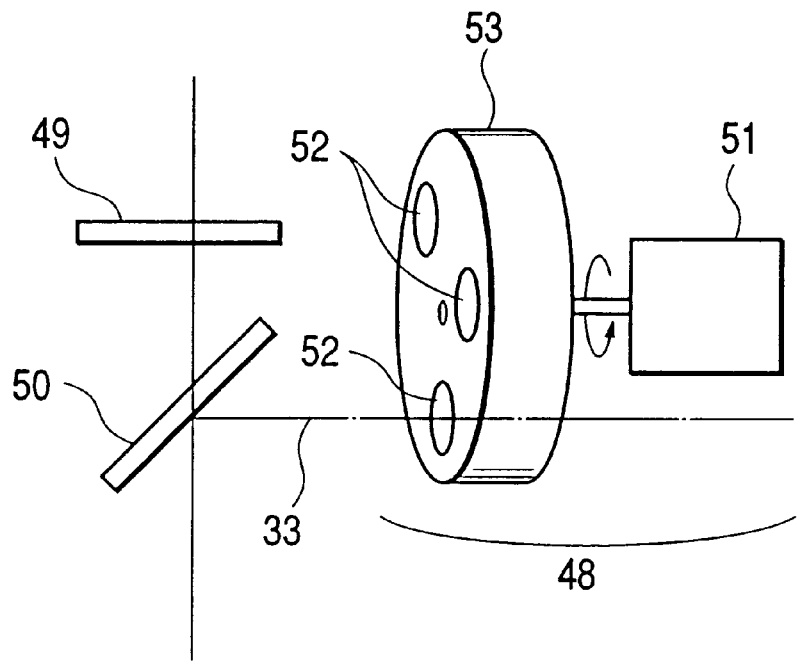
FIG. 19 shows a main part of the construction in the fifth embodiment of the fluorescence detecting device according to the present invention.
Figure 20:
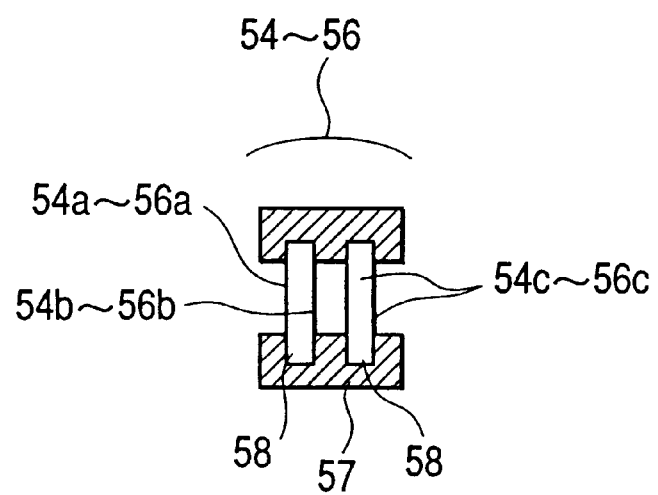
FIG. 20 shows a construction of the excitation filter set in the fifth embodiment.
Figure 21A:
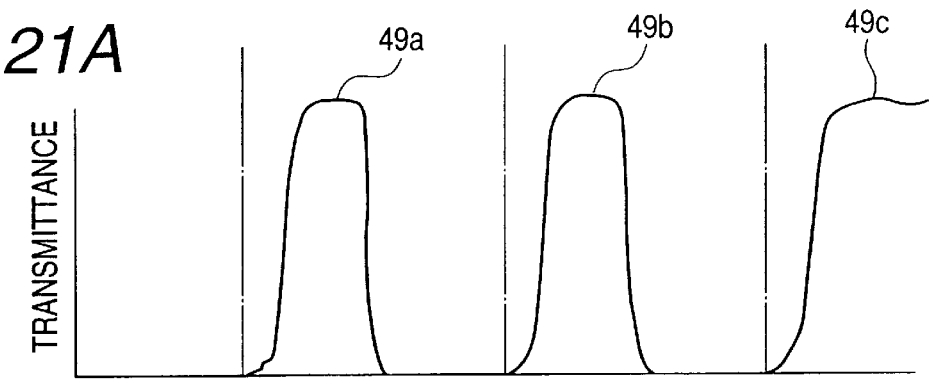
FIG. 21A shows transmittance spectra of the absorption filter set in the fifth embodiment.
Figure 21B:
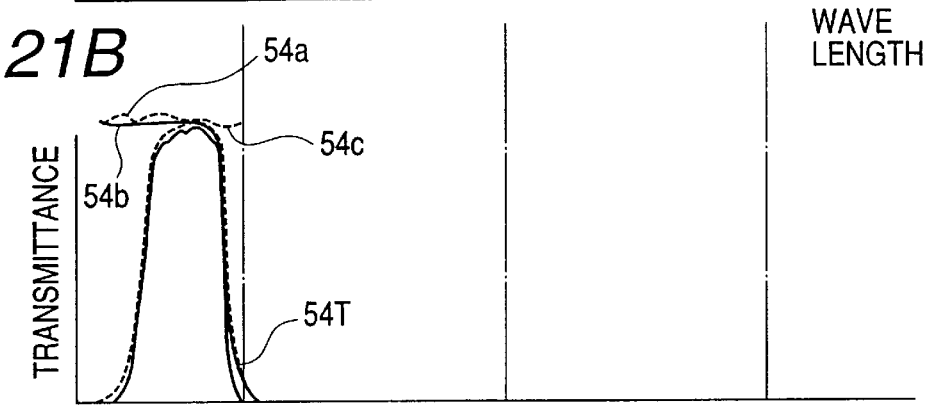
FIG. 21B shows transmittance spectra of the first excitation filter set in the fifth embodiment.
Figure 21C:
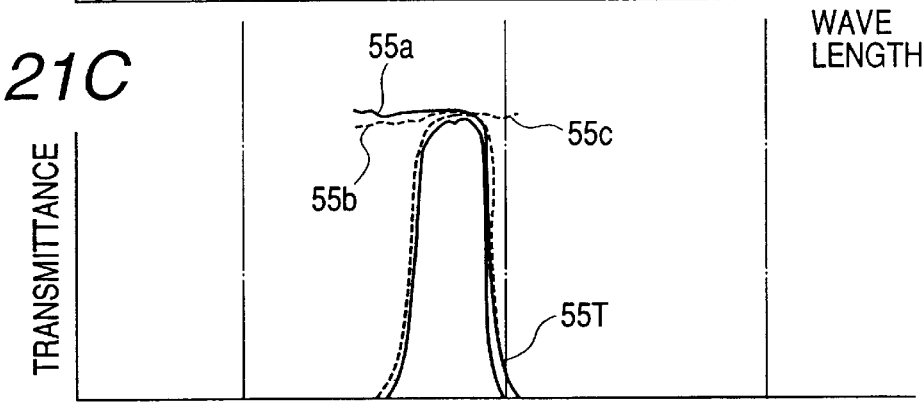
FIG. 21C shows transmittance spectra of the second excitation filter set in the fifth embodiment.
Figure 21D:
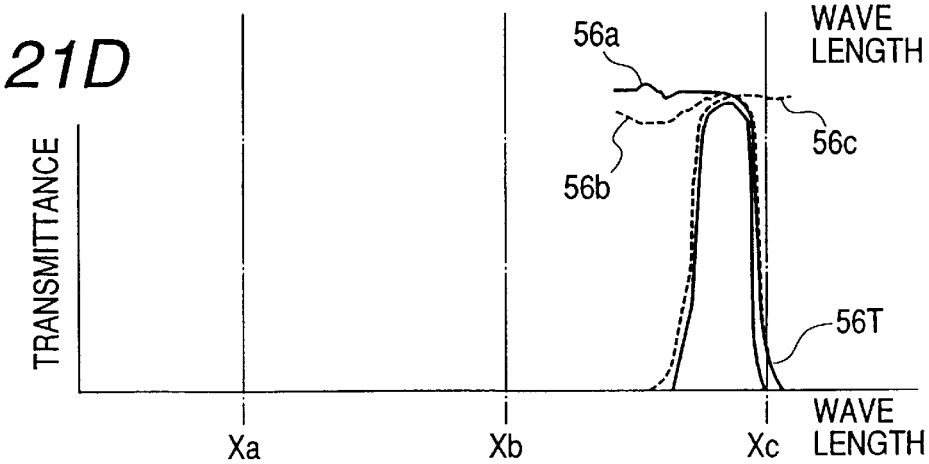
FIG. 21D shows transmittance spectra of the third excitation filter set in the fifth embodiment.

FIG. 19 shows a main part of the construction of the fifth embodiment according to the present invention, in which the other constructions are omitted since they have the same construction as shown in the first embodiment. FIG. 20 is a cross section indicating a part of the construction of the filter set holder. The reference numerals 48, 49 and 50 denote an excitation filter set, absorption filter set and dichroic mirror, respectively. The excitation filter set 48 is composed of a filter set rotation member 53 having three filter set holders 52 and a motor 51. The filter set rotation member 53 is disposed to allow rotation with the motor 51 around an axis line being a little tilted against the illumination optical axis, so that the center of each excitation filter of the three filter set holders 52 is able to align with the illumination optical axis 33. Three excitation filter sets 54, 55, 56 with different transmittance spectra with each other are inserted into the three filter set holders 52. Respective excitation filter sets 54, 55, 56 are composed of the interference film 54a, 54b, 54c; 55a, 55b, 55c; and 56a, 56b, 56c, respectively, formed on a glass substrate 58 attached to the filter frame 57.

Fluorescence is detected in the present embodiment by allowing the filter set rotation member 53 to rotate at a high speed. The illumination light is irradiated on the specimen 6 after converting its wavelength into three kinds of delayed excitation light wavelengths with the excitation filter sets 54, 55, 56. Fluorescence excited with the light having three kinds of excitation wavelengths pass through the dichroic mirror 50 with respective delayed timing and is detected after removing the illumination light with the absorption filter set 49. When switching of the excitation filter sets 54, 55, 56 is so rapid sufficiently beyond the resolution time of the detector, fluorescence luminous flux excited with the three kinds of the excitation filter sets 54, 55, 56 can be simultaneously detected.

FIGS. 21A, 21B, 21C and 21D show the transmittance spectra of the absorption filter set according to the present embodiment, of the excitation filter set 54, of the excitation filter set 55 and of the excitation filter set 56, respectively. The excitation transmission wavelength band 54T of the excitation filter set 54 is composed of the wavelength bands of the interference films 54a, 54b, 54c, the excitation transmission wavelength band 55T of the excitation filter set 55 is composed of the wavelength bands of the interference films 55a, 55b, 55c, and the excitation transmission wavelength band 56T of the excitation filter set 56 is composed of the wavelength bands of the interference films 56a, 56b, 56c. The filter set 49 has three fluorescence transmission wavelength bands 49a, 49b, 49c that allows fluorescent luminous flux excited with respective excitation light transmission wavelength bands 54T, 55T and 56T to transmit. The interference films 54a and 54b have a transmittance of 5% at the cross-over wavelength Xa between the excitation light transmission wavelength band 54T and the fluorescence transmission wavelength band 49a and a transmittance of 85% at a shorter wavelength from the wavelength Xa, the interference films 55a and 55b have a transmittance of 6% at the cross-over wavelength Xb between the excitation light transmission wavelength band 55T and the fluorescence transmission wavelength band 49b and a transmittance of 85% at a shorter wavelength from the wavelength Xb, and the interference films 56a and 56b have a transmittance of 3% at the cross-over wavelength Xc between the excitation light transmission wavelength band 56T and the fluorescence transmission wavelength band 49c and a transmittance of 90% at a shorter wavelength from the wavelength Xc. Accordingly, the fluorescence transmission wavelength bands 49a, 49b, 49c can be expanded toward the excitation wavelength side while excluding the illumination light wavelength by making rise-up of the transmittance from respective cross-over wavelengths of the filter sets 54, 55, 56 steep, enabling to quite effectively detect three kinds of fluorescent luminous flux with a high S/N ratio.

As hitherto described, a bright fluorescence image can be obtained with a very high S/N ratio by allowing the excitation light transmission wavelength band of the excitation filter set to ultimately come close to the fluorescence transmission wavelength band, providing an expensive and highly precise fluorescence detecting device without use of any filters.

What is claimed is:

1. A fluorescence detecting device comprising a light source, an illumination optical system for irradiating the light emitted from said light source to a specimen, an excitation filter set disposed in said illumination optical system for allowing a light with a specified wavelength region to transmit, a detecting optical system for detecting a fluorescence emitted from said specimen, and an absorption filter set disposed in the detecting optical system for allowing the fluorescence to transmit, wherein said excitation filter set includes at least two interference films with a transmittance of 25% or more at a wavelength by 20 nm shorter than the cross-over wavelength, and satisfies the following condition:

$$0.05\% < T < 10\%$$

where T denotes the transmittance of said interference film at said cross-over wavelength, and the cross-over wavelength is defined as a wavelength at the crossing point between the transmittance spectrum at a longer wavelength side of said excitation filter set and the transmittance spectrum at a shorter wavelength side of said absorption filter set.

2. A fluorescence detecting device comprising a light source, an illumination optical system for irradiating the light emitted from said light source to a specimen, an excitation filter set disposed in said illumination optical system for allowing a light with a specified wavelength region to transmit, a detecting optical system for detecting a fluorescence emitted from said specimen, and an absorption filter set disposed in the detecting optical system for allowing the fluorescence to transmit, wherein said absorption filter set includes at least two interference films with a transmittance of 50% or more at a wavelength by 20 nm longer than the cross-over wavelength, and satisfies the following condition:

$$0.05\% < T < 10\%$$

where T denotes the transmittance of said interference film at said cross-over wavelength, and the cross-over wavelength is defined as a wavelength at the crossing point between the transmittance spectrum at a longer wavelength side of said excitation filter set and the transmittance spectrum at a shorter wavelength side of said absorption filter set.

3. A fluorescence detecting device comprising a light source, an illumination optical system for irradiating the light emitted from said light source to a specimen, an excitation filter set disposed in said illumination optical system for allowing a light with a specified wavelength region to transmit, a detecting optical system for detecting a fluorescence emitted from said specimen, and an absorption filter set disposed in the detecting optical system for allowing the fluorescence to transmit, wherein said excitation filter set includes at least two first interference films with a transmittance of 25% or more at a wavelength by 20 nm shorter than the cross-over wavelength, said absorption filter set includes at least two second interference films with a transmittance of 50% or more at a wavelength by 20 nm longer than the cross-over wavelength, and said first and second interference films satisfy the following condition:

$$0.05\% < T < 10\%$$

where T denotes the transmittance of said interference film at said cross-over wavelength, and the cross-over wavelength is defined as a wavelength at the crossing point between the transmittance spectrum at a longer wavelength side of said excitation filter set and the transmittance spectrum at a shorter wavelength side of said absorption filter set.

4. A fluorescence detecting device comprising a monochromatic or semi-monochromatic light source, an illumination optical system for irradiating the light emitted from said light source to a specimen, a detecting optical system for detecting the fluorescence emitted from said specimen, and an absorption filter set disposed in said detecting optical system for allowing the fluorescence to transmit, wherein the shorter wavelength side of the fluorescence transmission wavelength band of said absorption filter set includes at least two interference films with a transmittance of 50% or more at a wavelength by 20 nm longer than the central wavelength of said light source, and satisfies the following condition:

$$0.05\% < T_1 < 10\%$$

where $T_1$ denotes the transmittance of said interference film at the central wavelength of said light source.

5. A fluorescence detecting device comprising a light source, an illumination optical system for irradiating the light emitted from said light source to a specimen, an excitation filter set disposed in said illumination optical system for allowing a light with a specified wavelength region to transmit, a detecting optical system for detecting a fluorescence emitted from said specimen, and an absorption filter set disposed in said detecting optical system for allowing the fluorescence to transmit, wherein said excitation filter set has a plurality of excitation light transmission wavelength bands $\tau_i$ (i=1, 2, ..., n), and said absorption filter set has a plurality of fluorescence transmission wavelength bands $E_i$ (i=1, 2, ..., n) corresponding to the excitation light transmission wavelength bands $\tau_i$, said excitation filter set including at least two interference films with a transmittance of 25% or more at a wavelength by 20 nm shorter than the cross-over wavelength $\lambda_i$ and satisfying the following condition:

$$0.05\% < T_i < 10\%$$

where $T_i$ denotes the transmittance of said interference film at said cross-over wavelength $\lambda_i$, and the cross-over wavelength $\lambda_i$ is defined as a wavelength at the crossing point between the transmittance spectrum at a longer wavelength side of an arbitrary excitation light transmission wavelength band $\tau_i$ and the transmittance spectrum at a shorter wavelength side of the fluorescence transmission wavelength band $E_i$.

6. A fluorescence detecting device comprising a light source, an illumination optical system for irradiating the light emitted from said light source to a specimen, an excitation filter set disposed in said illumination optical system for allowing a light with a specified wavelength region to transmit, a detecting optical system for detecting a fluorescence emitted from said specimen, and an absorption filter set disposed in said detecting optical system for allowing the fluorescence to transmit, wherein said excitation filter set has a plurality of excitation light transmission wavelength bands $\tau_i$ (i=1, 2, ..., n), and said absorption filter set has a plurality of fluorescence transmission wavelength bands $E_i$ (i=1, 2, ..., n) corresponding to the excitation light transmission wavelength bands $\tau_i$, said absorption filter set including at least two interference films with a transmittance of 50% or more at a wavelength by 20 nm longer than the cross-over wavelength $\lambda_i$ and satisfying the following condition:

$$0.05\% < T_i < 10\%$$

where $T_i$ denotes the transmittance of said interference film at said cross-over wavelength $\lambda_i$, and the cross-over wavelength $\lambda_i$ is defined as a wavelength at the crossing point between the transmittance spectrum at a longer wavelength side of an arbitrary excitation light transmission wavelength band $\tau_i$ and the transmittance spectrum at a shorter wavelength side of the fluorescence transmission wavelength band $E_i$.

7. A fluorescence detecting device comprising a light source, an illumination optical system for irradiating the light emitted from said light source to a specimen, an excitation filter set disposed in said the illumination optical system for allowing a light with a specified wavelength region to transmit, a detecting optical system for detecting a fluorescence emitted from said specimen, and an absorption filter set disposed in said detecting optical system for allowing the fluorescence to transmit, wherein said excitation filter set has a plurality of excitation light transmission wavelength bands $\tau_i$ (i=1, 2, ..., n), and said absorption filter set has a plurality of fluorescence transmission wavelength bands $E_i$ (i=1, 2, ..., n) corresponding to the excitation light transmission wavelength bands $\tau_i$, said excitation filter set including at least two first interference films with a transmittance of 25% or more at a wavelength by 20 nm shorter than the cross-over wavelength $\lambda_i$, said absorption filter set including at least two second interference films with a transmittance of 50% or more at a wavelength by 20 nm longer than the cross-over wavelength $\lambda_i$, and said first and second interference films satisfy the following condition:

$$0.05\% < T_i < 10\%$$

where $T_i$ denotes the transmittance of said interference film at said cross-over wavelength $\lambda_i$, and the cross-over wavelength $\lambda_i$ is defined as a wavelength at the crossing point between the transmittance spectrum at a longer wavelength side of an arbitrary excitation light transmission wavelength band $\tau_i$ and the transmittance spectrum at a shorter wavelength side of the fluorescence transmission wavelength band $E_i$.

8. A fluorescence detecting device comprising a light source, an illumination optical system for irradiating the light emitted from said light source to a specimen, an excitation filter set disposed in said illumination optical system for allowing a light with a specified wavelength region to transmit, a detecting optical system for detecting a fluorescence emitted from said specimen, and an absorption filter set disposed in said detecting optical system for allowing the fluorescence to transmit, wherein said excitation filter set has a plurality of excitation light transmission wavelength bands $\tau_i$ (i=1, 2, ..., n), and said absorption filter set has a plurality of fluorescence transmission wavelength bands $E_i$ (i=1, 2, ..., n) corresponding to the excitation light transmission wavelength bands $\tau_i$, said excitation filter set including at least two interference films with a transmittance of 25% or more at a wavelength by 20 nm longer than the cross-over wavelength $\lambda_i'$, and said interference films satisfy the following condition:

$$0.05\% < T_i' < 10\%$$

where $T_i'$ denotes the transmittance of said interference film at said cross-over wavelength $\lambda_i'$, and the cross-over wavelength $\lambda_i'$ is defined as a wavelength at the crossing point between the transmittance spectrum at a shorter wavelength side of an arbitrary excitation light transmission wavelength band $\tau_i+1$ and the transmittance spectrum at a longer wavelength side of the fluorescence transmission wavelength band $E_i$.

9. A fluorescence detecting device comprising a light source, an illumination optical system for irradiating the light emitted from said light source to a specimen, an excitation filter set disposed in said illumination optical system for allowing a light with a specified wavelength region to transmit, a detecting optical system for detecting a fluorescence emitted from said specimen, and an absorption filter set disposed in said detecting optical system for allowing the fluorescence to transmit, wherein said excitation filter set has a plurality of excitation light transmission wavelength bands $\tau_i$ (i=1, 2, ..., n), and said absorption filter set has a plurality of fluorescence transmission wavelength bands $E_i$ (i=1, 2, ..., n) corresponding to the excitation light transmission wavelength bands $\tau_i$, said absorption filter set including at least two interference films with a transmittance of 50% or more at a wavelength by 20 nm shorter than the cross-over wavelength $\lambda_i'$, and said interference films satisfy the following condition:

$$0.05\% < T'_i < 10\%$$

where $T'_i$ denotes the transmittance of said interference film at said cross-over wavelength $\lambda'_i$, and the cross-over wavelength $\lambda'_i$ is defined as a wavelength at the crossing point between the transmittance spectrum at a shorter wavelength side of an arbitrary excitation light transmission wavelength band $\tau_i+1$ and the transmittance spectrum at a longer wavelength of the fluorescence transmission wavelength band $E_i$.

10. A fluorescence detecting device comprising a light source, an illumination optical system for irradiating the light emitted from said light source to a specimen, an excitation filter set disposed in said illumination optical system for allowing a light with a specified wavelength region to transmit, a detecting optical system for detecting a fluorescence emitted from said specimen, and an absorption filter set disposed in said detecting optical system for allowing the fluorescence to transmit, wherein said excitation filter set has a plurality of excitation light transmission wavelength bands $\tau_i$ (i=1, 2, ..., n), and said absorption filter set has a plurality of fluorescence transmission wavelength bands $E_i$ (i=1, 2, ..., n) corresponding to the excitation light transmission wavelength bands $\tau_i$, said excitation filter set including at least two first interference films with a transmittance of 25% or more at a wavelength by 20 nm longer than the cross-over wavelength $\lambda'_i$, said absorption filter set including at least two second interference films with a transmittance of 50% or more at a wavelength by 20 nm shorter than the cross-over wavelength $\lambda'_i$, and said first and second interference films satisfy the following condition:

$$0.05\% < T'_i < 10\%$$

where $T'_i$ denotes the transmittance of said interference film at said cross-over wavelength $\lambda'_i$, and the cross-over wavelength $\lambda'_i$ is defined as a wavelength at the crossing point between the transmittance spectrum at a shorter wavelength of an arbitrary excitation light transmission wavelength band $\tau_i+1$ and the transmittance spectrum at a longer wavelength of the fluorescence transmission wavelength band $E_i$.

11. A fluorescence detecting device comprising a monochromatic or semi-monochromatic light source, an illumination optical system for irradiating the light emitted from said light source to a specimen, a detecting optical system for detecting a fluorescence emitted from said specimen, and an absorption filter set disposed in said detecting optical system for allowing the fluorescence to transmit, wherein said light source emits a light with a plurality of central wavelengths of $\lambda 1_j$ (j=1, 2, ..., n), and said absorption filter set has a plurality of fluorescence transmission wavelength bands $E_j$ (j=1, 2, ..., n) corresponding to the central wavelength $\lambda 1_j$ of said light source, the shorter wavelength side of the fluorescence transmission wavelength bands $E_j$ of said absorption filter set including at least two interference films with a transmittance of 50% or more at a wavelength by 20 nm longer than the central wavelength $\lambda 1_j$ of said light source and satisfying the following condition:

$$0.05\% < T1_j < 10\%$$

where $T1_j$ denotes the transmittance of the interference film at the central wavelengths of said light source.

12. A fluorescence detecting device comprising a monochromatic or semi-monochromatic light source, an illumination optical system for irradiating the light emitted from said light source to a specimen, a detecting optical system for detecting a fluorescence emitted from said specimen, and an absorption filter set disposed in said detecting optical system for allowing the fluorescence to transmit, wherein said light source emits a light with a plurality of central wavelengths of $\lambda 1_j$ (j=1, 2, ..., n), and said absorption filter set has a plurality of fluorescence transmission wavelength bands $E_j$ (j=1, 2, ..., n), corresponding to the central wavelength $\lambda 1_j$ of said light source, the longer wavelength side of the fluorescence transmission wavelength bands $E_j$ of said absorption filter set including at least two interference films with a transmittance of 50% or more at a wavelength by 20 nm shorter than the central wavelength $\lambda 1_j+1$ of said light source and satisfying the following condition:

$$0.05\% < T'1_j < 10\%$$

where $T'1_j$ denotes the transmittance of the interference film at the central wavelength of said light source.

13. A fluorescence detecting device according to any one of claims 1 to 4, wherein at least one of the interference films are disposed by being tilted against the plane perpendicular to the optical axis.

14. A fluorescence detecting device according to claim 13, wherein the interference film is formed on a transparent substrate adjustably mounted on the device.

15. A fluorescence detecting device according to any one of claims 1 to 12, wherein the interference film is disposed in non-parallel relations with each other.

16. A fluorescence detecting device according to any one of claims 1 to 4, wherein the interference film satisfies the condition of $0.1\% < T'' < 5\%$ when $T''$ is defined to be the transmittance of the interference film at the cross-over wavelength or at the central wavelength of said light source.

* * * * *